United States Patent
Andre et al.

(10) Patent No.: US 6,409,735 B1
(45) Date of Patent: Jun. 25, 2002

(54) DEVICE FOR POSITIONING SURGICAL INSTRUMENTS

(75) Inventors: Jacques Andre, Waterloo; Jean Mangez, Namur; Xavier Moreels, Gembloux; Roland Polet, Tervuren, all of (BE)

(73) Assignee: Medsys S.A., Gembloux (BE)

( * ) Notice: Subject to any disclaimer, the term of this patent is extended or adjusted under 35 U.S.C. 154(b) by 0 days.

(21) Appl. No.: 09/554,519

(22) PCT Filed: Nov. 16, 1998

(86) PCT No.: PCT/BE98/00177
§ 371 (c)(1),
(2), (4) Date: Jul. 14, 2000

(87) PCT Pub. No.: WO99/25267
PCT Pub. Date: May 27, 1999

(30) Foreign Application Priority Data

Nov. 14, 1997 (EP) .............................. 97870183

(51) Int. Cl.⁷ .............................................. A61B 19/00
(52) U.S. Cl. .................................................... 606/130
(58) Field of Search ......................... 606/130; 600/114, 600/227, 228, 229

(56) References Cited

U.S. PATENT DOCUMENTS

| | | | |
|---|---|---|---|
| 5,240,011 A | * 8/1993 | Assa ....................... | 606/130 X |
| 5,273,039 A | * 12/1993 | Fujiwara et al. ........ | 606/130 X |
| 5,397,323 A | * 3/1995 | Taylor et al. ............. | 606/130 |
| 5,441,042 A | 8/1995 | Putman | |
| 5,441,505 A | * 8/1995 | Nakamura ................. | 606/130 |
| 5,540,649 A | 7/1996 | Bonnell et al. | |
| 5,571,072 A | 11/1996 | Kronner | |
| 5,697,939 A | * 12/1997 | Kubota et al. ............. | 606/130 |

FOREIGN PATENT DOCUMENTS

| | | |
|---|---|---|
| EP | 0 293 227 A2 | 11/1988 |
| EP | 0 293 760 A2 | 12/1988 |
| EP | 0 752 237 A1 | 1/1997 |
| WO | WO 94/26167 | 11/1994 |
| WO | WO 95/10389 | 4/1995 |
| WO | WO 95/16396 | 6/1995 |

* cited by examiner

*Primary Examiner*—Jeffrey A. Smith
(74) *Attorney, Agent, or Firm*—Knobbe, Martens, Olson & Bear, LLP (57) ABSTRACT

The invention concerns a device for positioning a surgical instrument, characterized in that it comprises a fixed support combined with at least: a first mobile element articulated on the fixed support about a first axis substantially parallel to the plane wherein the patient is placed and capable of carrying out a first movement; a second mobile element articulated at the end of the first element about a second axis substantially parallel to the plane wherein the patient is placed and capable of carrying out a second movement; a deformable element fixed on one side to the end of the second mobile element and capable of carrying out a third rotating movement about a third axis; a prehensile member fixed on the side opposite to that of the second element to the deformable element; a device for locking a surgical instrument on the prehensile member; and actuating means for producing the rotating movements about the different axes.

11 Claims, 11 Drawing Sheets

DEVICE FOR POSITIONING SURGICAL INSTRUMENTS

FIELD OF THE INVENTION

The present invention relates to a device which allows surgical instruments, such as an endoscope, to be handled, that is to say positioned and displaced, during a surgical operation.

BACKGROUND OF THE INVENTION

For many years there have been aids taking the form of mechanical devices capable of carrying surgical instruments intended for assisting the surgeon during operations.

Improvements have been made to these aids, so that these devices can be displaced and can, where appropriate, actuate these surgical instruments, particularly scopes.

These devices are essentially intended for keeping the surgeon's hands free, so that he no longer has to break off performing an act in order, for example, to displace the scope or has to entrust the handling of the latter to an assistant.

However, most of the various known devices do not afford accuracy in the positioning of the instrument and stability in holding and/or displacing it which are sufficient for uses in the medical field, such as surgical acts.

In particular, an endoscope stabilization device is known, as published in the document U.S. Pat. No. 5,184,601, which comprises an independent bracket provided with a multiple-axis robot which makes it possible to execute rotational movements about vertical axes in order to cover a horizontal plane (XY) parallel to the patient. This device has the disadvantages of requiring a combination of a plurality of movements, in order to displace a scope in the directions and orientations desired by the surgeon, and of obstructing the surgeon's range of action by the presence of arms which are displaced in the horizontal plane (XY) above the patient.

The document WO94/26167 also discloses a positioning device intended for carrying an instrument for laparoscopic surgery uses which provides a spherical centre of rotation of the said instrument, this centre being formed, for example, by the point of penetration into the patient's stomach. It is found, however, that this device will not make it possible to execute a translational movement along the axis of the instrument, which movement must be made possible so that a scope can be used.

The document WO95/16396 describes a device for the handling of a surgical instrument with the aid of a plurality of successive arms which execute rotations about vertical axes, as proposed above, the device making it possible to obtain an incremental displacement of the head of the scope as a result of a complex and detailed calculation of the various movements of the actuators. However, these movements are obtained by means of three successive changes of Cartesian co-ordinates, thus making the display of the movements relatively complex. In order to provide a decision-making aid to the handling of the instrument, a voice control may also be proposed. This voice control does not, however, make it possible to carry out small rapid and/or high-rate displacements.

The documents EP-A-0293760 and U.S. Pat. No. 5,540,649 relate to the same handling device which comprises a vertical foot experiencing a first vertical rotational movement. The second movement is a rotation along an axis orthogonal to the vertical axis. This makes it possible to carry out a displacement of the entire device over the patient himself, thus limiting the surgeon's range of action.

SUMMARY OF THE INVENTION

The present invention aims to propose a device for the handling of surgical instruments which is of relatively simple design and has the smallest possible overall size.

Another object of the present invention is to propose a device which as far as possible allows the surgeon's hands to be kept free.

Another object of the present invention is as far as possible to reduce the obstruction of the surgeon's field of action.

Another object of the present invention is to propose a device which makes it possible to have a combination of simple movements reproducing the three fundamental movements involved in exploring the field of vision.

Another object of the present invention is to propose a control device which is simple and of very small overall size, such that it allows other instruments to be handled.

Other objects and advantages will be gathered from a reading of the following descriptive note.

The present invention relates to a device for the handling of a surgical instrument, said device being composed of a fixed support element associated with at least:

- a first moveable element articulated on the fixed support element about a first axis essentially parallel to the plane in which the patient is arranged, thus generating a first movement;
- a second moveable element articulated on the end of the first element about a second axis essentially parallel to the plane in which the patient is arranged, thus generating a second movement;
- a deformable third element fastened on one side to the end of the second moveable element and capable of executing a third rotational movement about a third axis;
- a gripping element fastened to the deformable element on the opposite side to that of the second element;
- a device for securing a surgical instrument to the gripping element; and
- action means making it possible to execute rotational movements about the various axes.

This means, in general terms, that the first and second movements take place about essentially horizontal axes, particularly when the plane in which the patient is arranged is itself horizontal. Preferably, the two horizontal axes are parallel to one another, and their projections in the plane of the patient are orthogonal to the axis of the patient.

Preferably, the first and second moveable elements take the form of articulated arms, whilst the deformable element takes the form of a deformable and articulated quadrilateral.

The second articulated moveable element has two points of articulation, one of which can slide in a slideway and the other of which can be blocked or free.

According to a particular embodiment, the gripping element is arranged in a slideway integral with the deformable element.

The support element is fastened to a rail integral with the operating table with the aid of a fastening device.

According to a first embodiment, this fastening device comprises at least two boxes which execute a first movement orthogonal to the patient's bed and a longitudinal second movement parallel to the patient's bed. A screw makes it possible to carry out the movement of the first box in the second box so as to obtain the first movement which is orthogonal to the patient's bed. The second movement, which is longitudinal, is carried out with the aid of a third box which comprises rolling bearings which slide on a slideway. The fastening of the device is carried out when one or more screws are tightened, the rail at the same time being clamped between the clamps and a suitable element.

According to another embodiment, the longitudinal movement is carried out with the aid of a plurality of, preferably four rolling bearings using the rail of the operating table as a slideway, a lower clamp making it possible by means of a handwheel to immobilize the assembly as a whole on the said rail.

The fastening device may be reversed by rotation about a vertical axis and is adjusted by sliding along the fastening rail integral with the operating table.

Moreover, according to a preferred embodiment, the handling device comprises a control device which consists of a mini-keyboard with at least six keys for two or three fingers and the inner part of which is of triangular shape. This control device is completely independent and comprises a transmitter which transmits the commands to the main case, this transmitter taking the form of a small case of triangular shape.

DESCRIPTION OF SEVERAL PREFERRED EMBODIMENTS OF THE INVENTION

Figure 1:
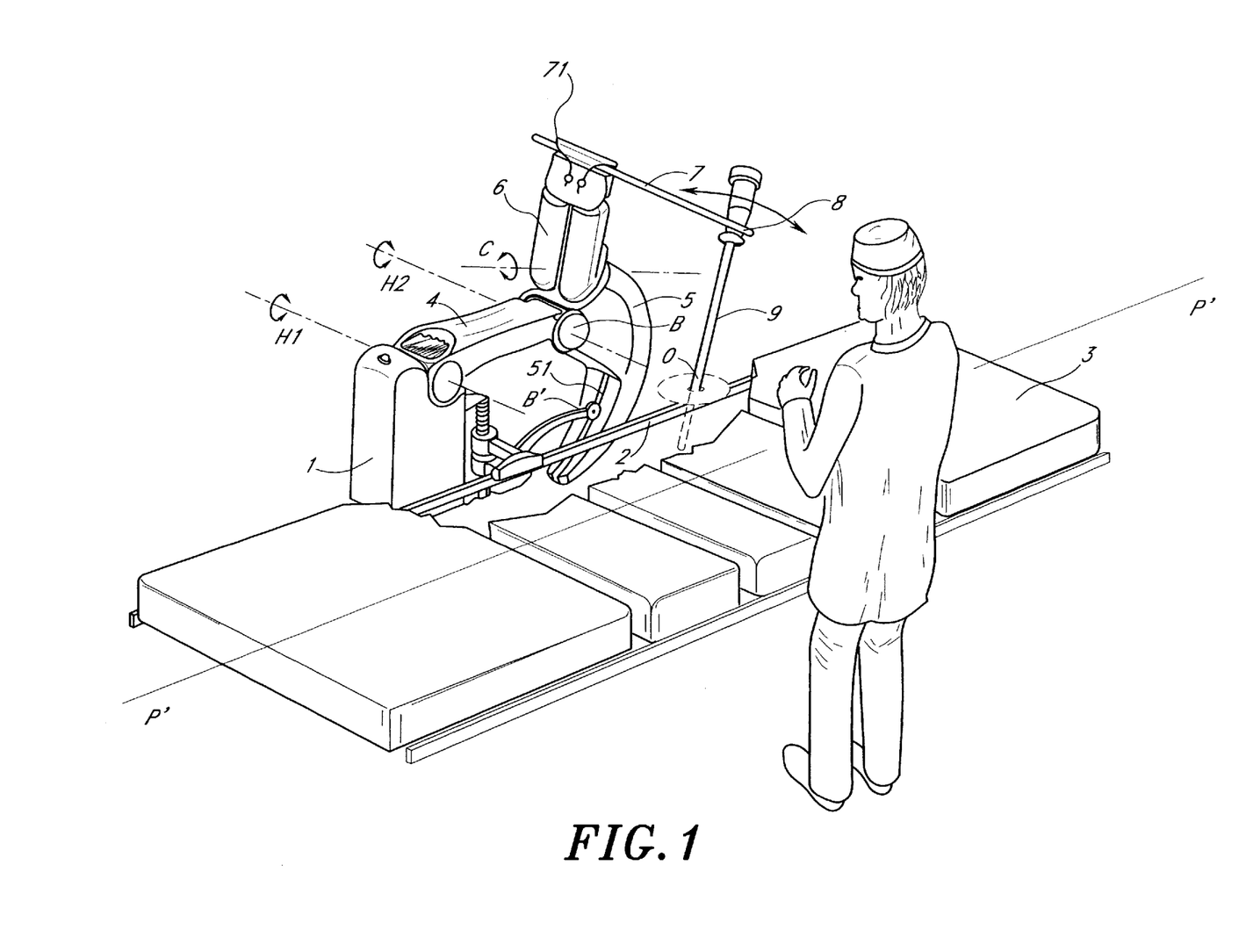
FIG. 1 shows a perspective view of the operating table, on which the patient will be laid and to which the handling device according to the present invention is fastened.

The handling device according to the present invention is shown in FIG. 1 in perspective and is integral with the bed on which the patient will lie down.

The particular advantage of this handling device is that it possesses a range of displacement such that it can be used for two large groups of surgical operations: on the one hand, gynaecological surgical operations and, on the other hand, abdominal surgical operations. It is sufficient, in order to change from one area to the other, simply to overturn the appliance in relation to a vertical plane perpendicular to the axis along which the patient is laid. This means that the appliance is, of course, reversible and that it is sufficient to orient it in the front or rear position in relation to the patient.

Figure 2:
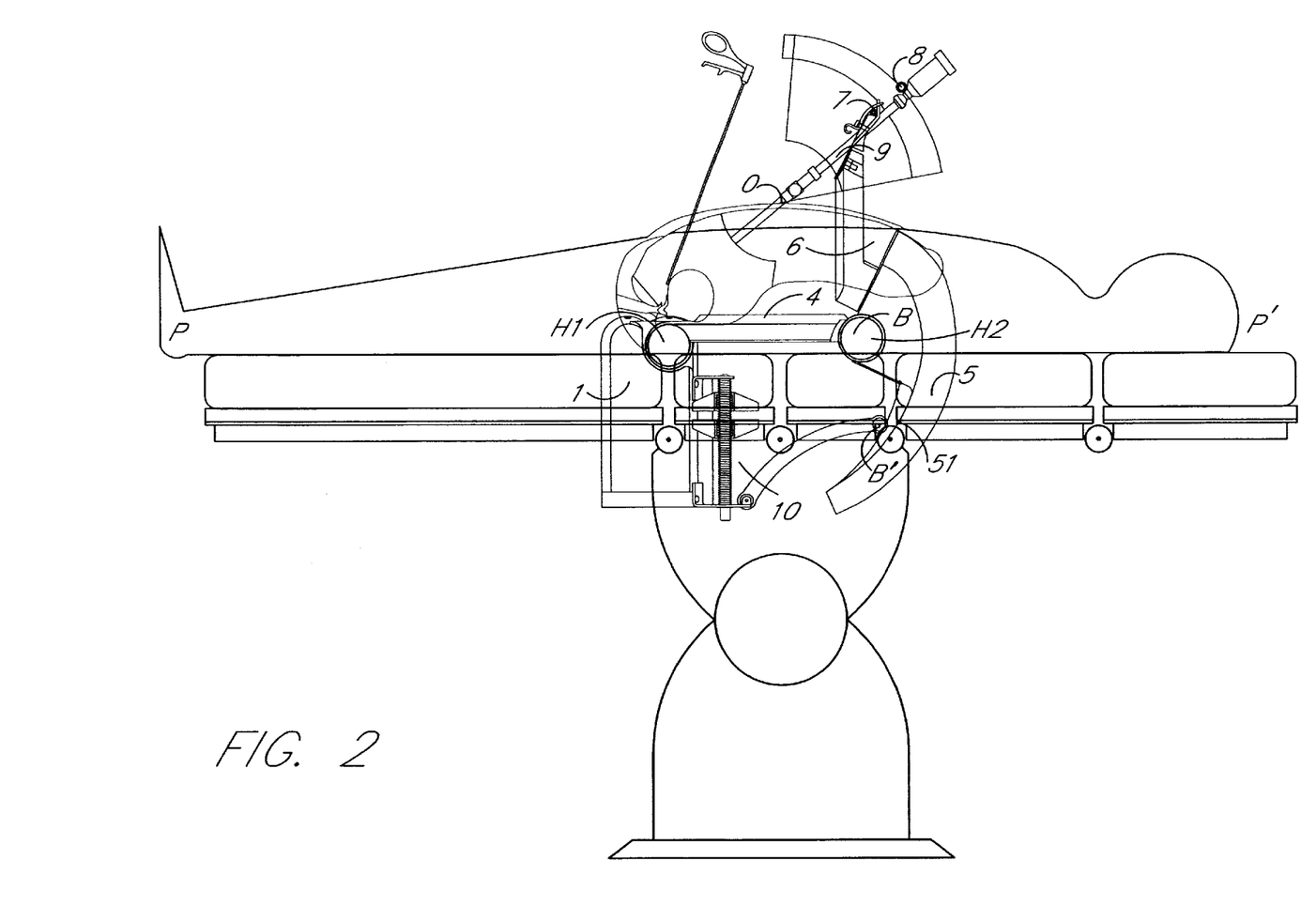
FIGS. 2 and 3 show a sectional side view of the device for the handling of surgical instruments according to the present invention, for two uses in surgical operations.

FIG. 2 more specifically shows the device arranged so as to make it possible to carry out an operation of a gynaecological nature. This means essentially that the endoscope will penetrate into the patient in a position such that it makes it possible to obtain a display of the area where the surgeon will have to operate.

Figure 3:
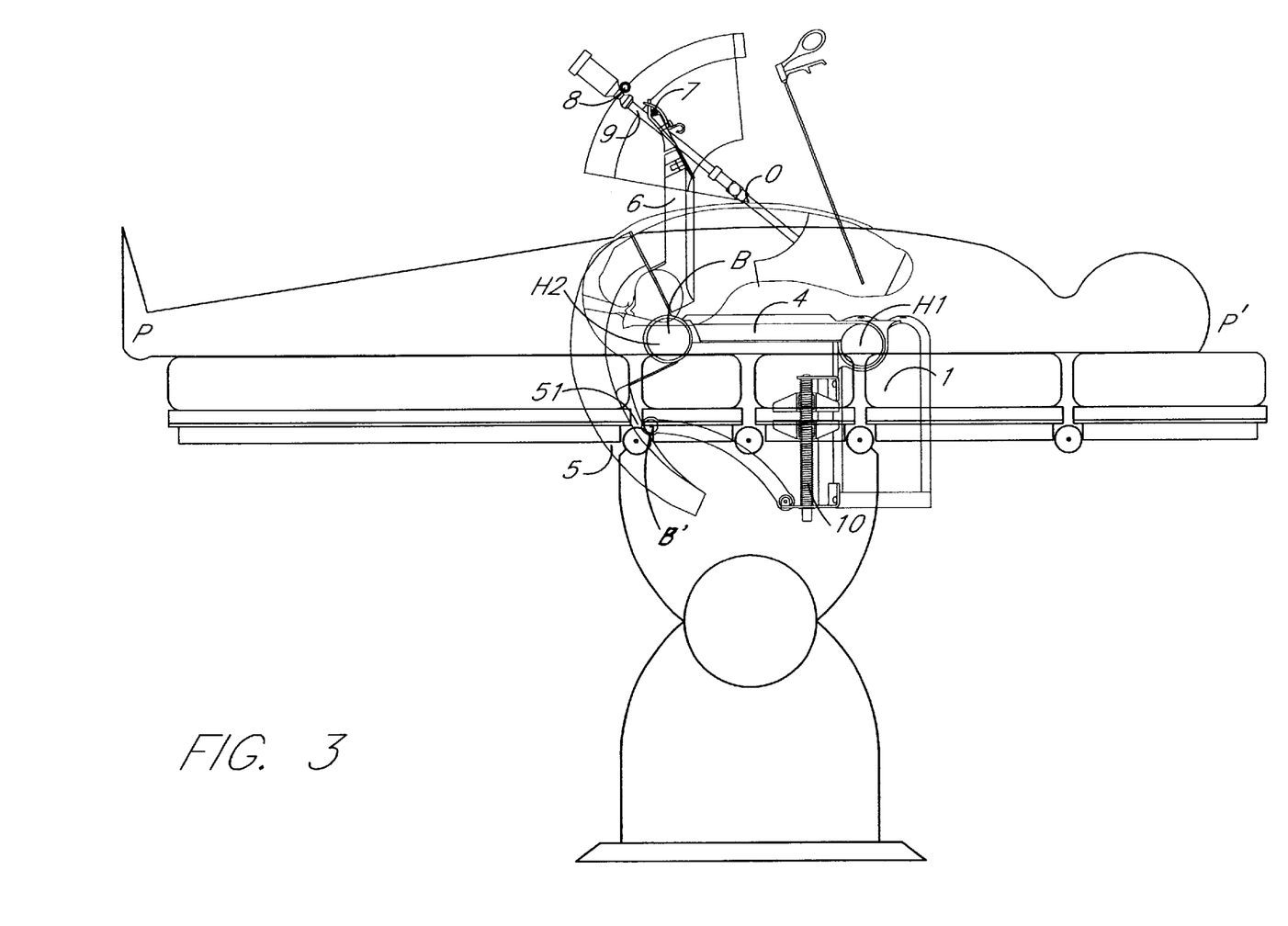
Figure 4:
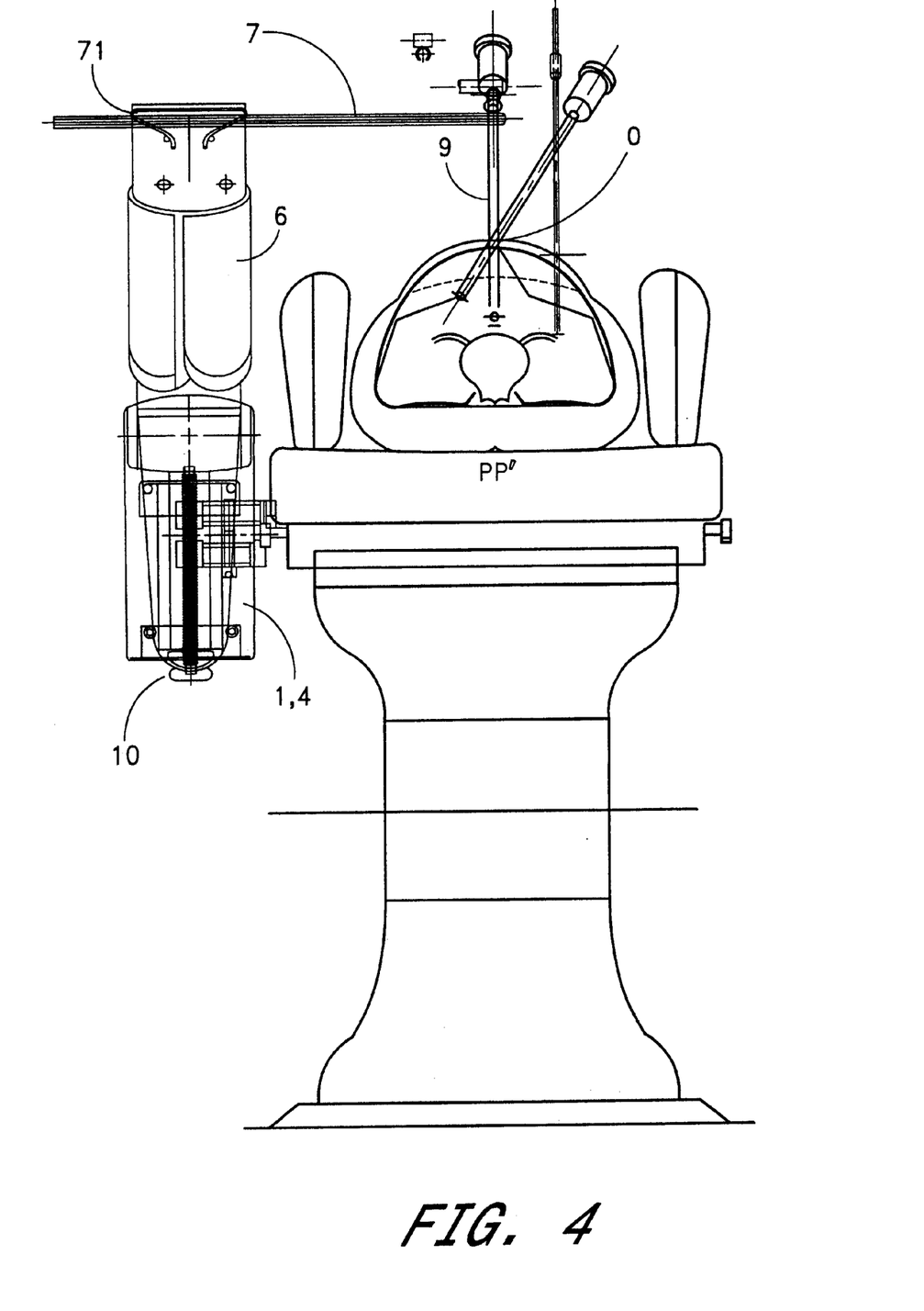
FIGS. 4 and 5 show sectional front views of the device, as shown in FIGS. 2 and 3.
Figure 5:
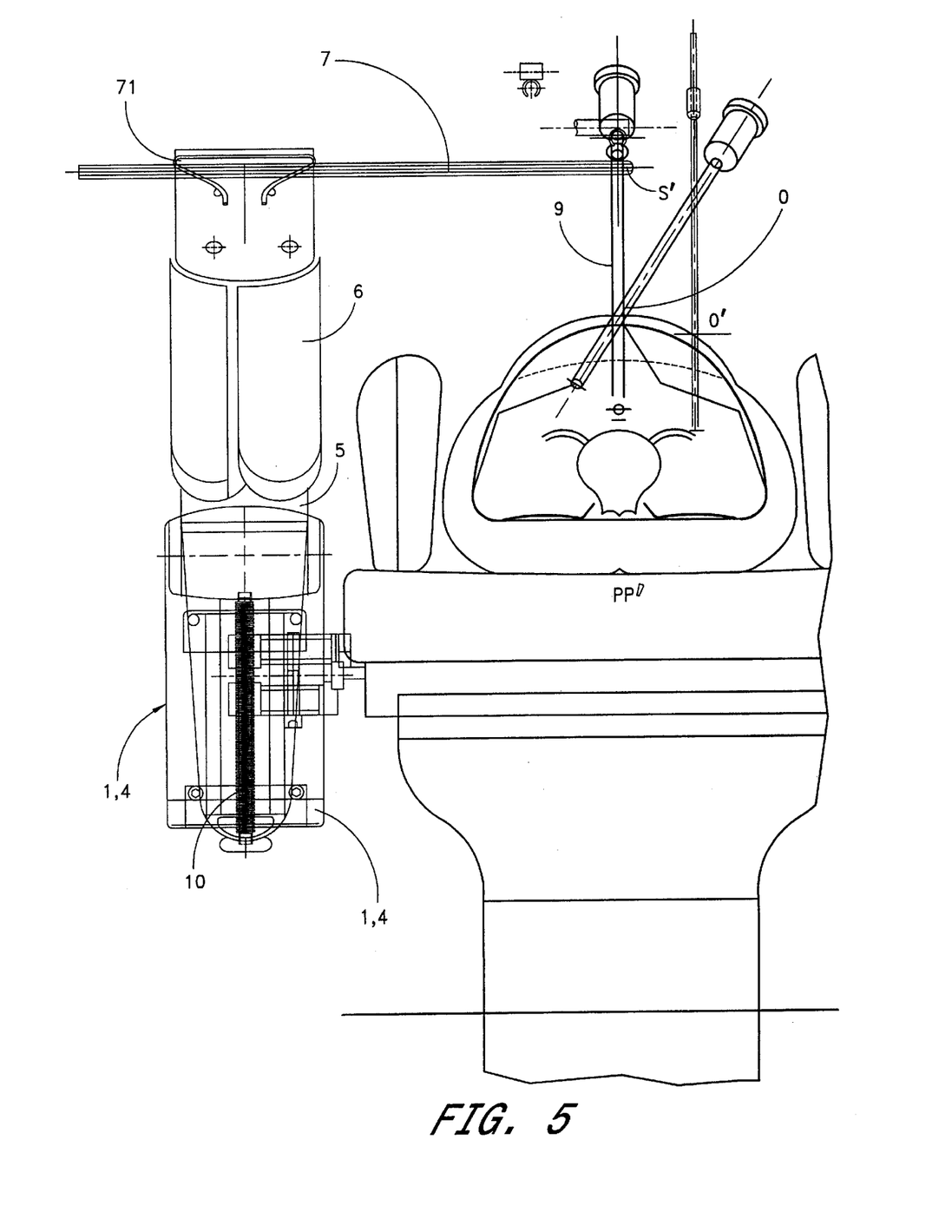

FIG. 3 shows the device arranged so as to make it possible to carry out an operation of an abdominal nature. In this case, the endoscope will penetrate into the patient in a position such that it makes it possible to have a display towards the patient's head.

Other kinds of surgical operations, such as orthopaedic operations, are also conceivable.

In FIGS. 1 to 6, the patient's body is arranged along an axis PP', with the patient's head directed towards P'. 0 represents the point of penetration of the instrument into the patient's stomach. This point generally represents the patient's navel.

As is apparent from the various Figures, this handling device comprises at least the following elements:

a support (1) (after vertical and longitudinal adjustment) will be fastened to a rail (2) integral with the operating table (3), this fastened support being associated with:

a first moveable arm (4) articulated on the fastened support about an essentially horizontal axis Hi perpendicular to the vertical plane passing through the longitudinal axis POP, of the patient;

a second moveable arm (5) articulated on the end of the first arm about a second essentially horizontal axis H2, likewise perpendicular to the same plane POP';

a deformable element (6) fastened on one side to the end of the second arm (5) and capable of executing a rotational movement about an axis C;

a horizontal gripping arm (7) fastened to the opposite side of the quadrilateral (6);

a device (8) for securing an instrument (9) to the gripping arm (7);

actuators which make it possible to execute rotational movements about the various axes H1, H2 and C mentioned;

means for controlling and synchronizing these movements; and a control placed in the palm of the practitioner's hand, enabling him to have access to the various movements by means of a plurality of keys.

The handling device thus makes it possible to displace an instrument (9) by means of movements about two axes of rotation (H1 and H2), parallel to one another and to the patient's bed, and about a third axis of rotation (C).

It can be seen that, according to the present invention, the first rotational movement does not take place about an axis which is perpendicular to the operating table and which, more particularly, is vertical. This thereby makes it possible for the surgeon's range of action to be kept free in a particularly advantageous way.

The combination of the movements makes it possible to obtain the three fundamental movements for exploring the field of vision, as are shown in Table 1.

TABLE 1

| | Movement imparted to the scope | | |
|---|---|---|---|
| Eye movements | Guidance | Direction | Symbol (+ direction) |
| Accommodation (near/far) | Zoom | in/out | $\zeta$ (i/o) |
| Vertical rotation (up/down) | Rotation | up/down | $\rho$ (u/d) |
| Horizontal rotation (left/right) | Lateral | left/right | $\lambda$ (l/r) |

The movements produced will therefore correspond to:

$\zeta$(i/o): displacement along the axis of the scope (SS')

$\rho$ (u/d): rotation of the scope in the plane POP' about 0.

$\lambda$ (l/r): rotation of the scope in the plane S'00' about 0.

Figure 6:
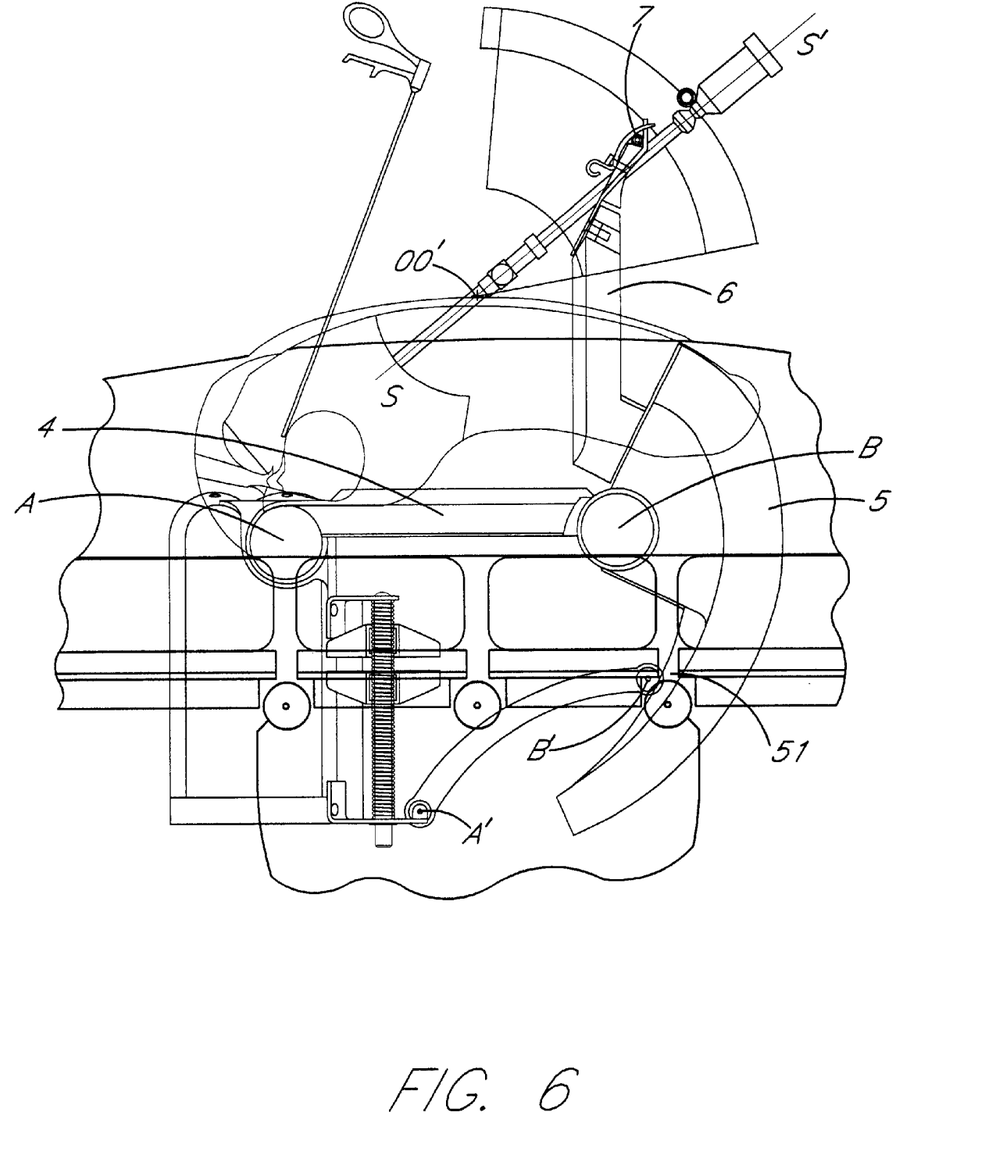
FIG. 6 shows a sectional side view corresponding to that of FIG. 2, but making it possible to visualize the various movements of the handling device.

Preferably, the second arm (5), for its part, takes the form of one of the sides (BB') of an articulated parallelogram (ABB'A'), as shown in more detail in FIG. 6. The point of articulation (B') can slide along a slideway (51) integral with the arm (5); the position relative to the arm (5) and the length of the arm (BB') may therefore vary.

Two illustrative situations may arise:

the point of articulation (B) is blocked; the arms and elements (5, 6 and 7) are therefore simply driven about the axis H1 as a result of the rotation of the support (1), and the movement of S' and S is therefore close to ρ:

the point of articulation (B) is free, but the position of (B') in its slideway is blocked by a solenoid: in this case, the movement of the parallelogram (6) driven about the axis H1 as a result of the rotation of the support (1) induces a displacement in the gripping arm (7), and therefore of S' and S, which is close to ς.

This embodiment makes it possible to ensure the movements ρ and ς by means of a single servomotor.

The gripping arm (7) is always horizontal. This makes it possible to limit to the maximum the obstruction caused by the latter in the surgeon's range of action. It is connected to the mechanism and to the patient's bed on the opposite side to the surgeon.

The surgical instrument (9), such as an endoscope, is connected to the gripping arm (7) by means of a passive (non-motorized) joint, so as to reproduce the image which it perceives, and in such a way that it is always oriented correctly relative to the reference axes of the room, that is to say the vertical directions must appear vertical on the monitor. The rotation of the second arm (5) and the deformation of the articulated parallelogram (6) are ensured by two servomotors incorporated in the arm (5).

The fastening of the scope (9) to the gripping arm (7) at S' may be ensured by means of a passive joint consisting at least of two components articulated along the axis perpendicular to the axis of the gripping arm (7) and to SS'.

The component holding the scope is fastened to the latter in a position such that the verticality reference of the image is in the vertical plane passing through the axis perpendicular to the axis of the gripping arm (7) and SS'. The image of the scope will thus appear vertical to an imaginary observer situated at the patient's head and looking parallel to the axis PP'.

The component secured to the gripping arm (7) at S' is snapped onto this gripping arm (7) so as to be capable of rotating freely about the axis (d). This component is designed to be capable of being unsnapped from the gripping arm (7) simply by action on a small lever.

Alternatively, this assembly may usefully be produced in one piece from an elastic material.

Figure 12:
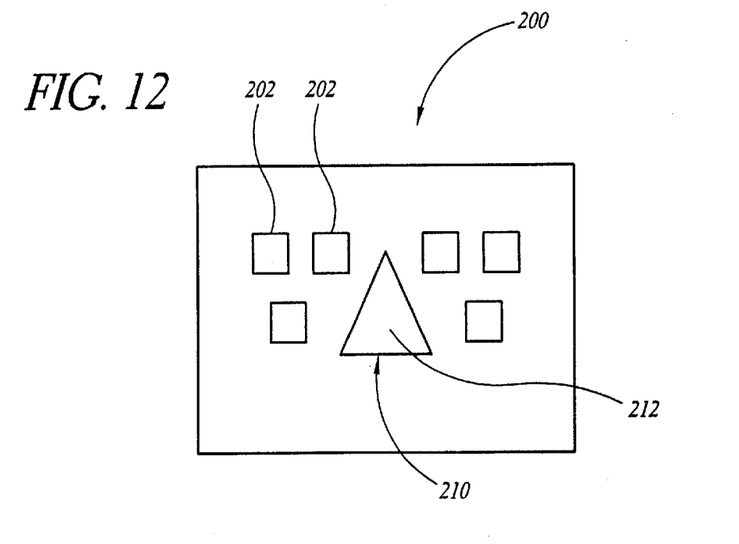
FIG. 12 shows an independent control device of the handling device consisting of a mini-keyboard.

The control device of the handling device may consist of a mini-keyboard (200) with six keys (202) for two or three fingers (little finger and ring finger, plus the middle finger in the case of the three-finger version) placed in the palm of the practitioner's hand by means of a suitable holder surrounding the practitioner's hand, characterized in that the inner part (210) (in the palm of the hand) of triangular shape (212) is inscribed within the "trapezium" of the hand between the ball of the thumb and the fold of the four fingers, thus in no way impeding the movements of the hand.

Preferably, the arm (7) gripping the instrument (9) can be adjusted in a slideway (71), so as to arrange S' and therefore S in such a way that they are located in the plane POP'. This constitutes the adjustment of the neutral point of S at the start of the operation. By virtue of this particular feature, the handling device can be adapted to one type of operation or the other: abdominal or gynaecological (see FIGS. 1 and 2), simply by rotating the fastening device through 180°, reversing it and then adjusting the gripping arm (7) in its slideway (71).

In general terms, the handling device is fastened to a rail (2), itself integral with the operating table (3), with the aid of a fastening device (100).

Figure 7:
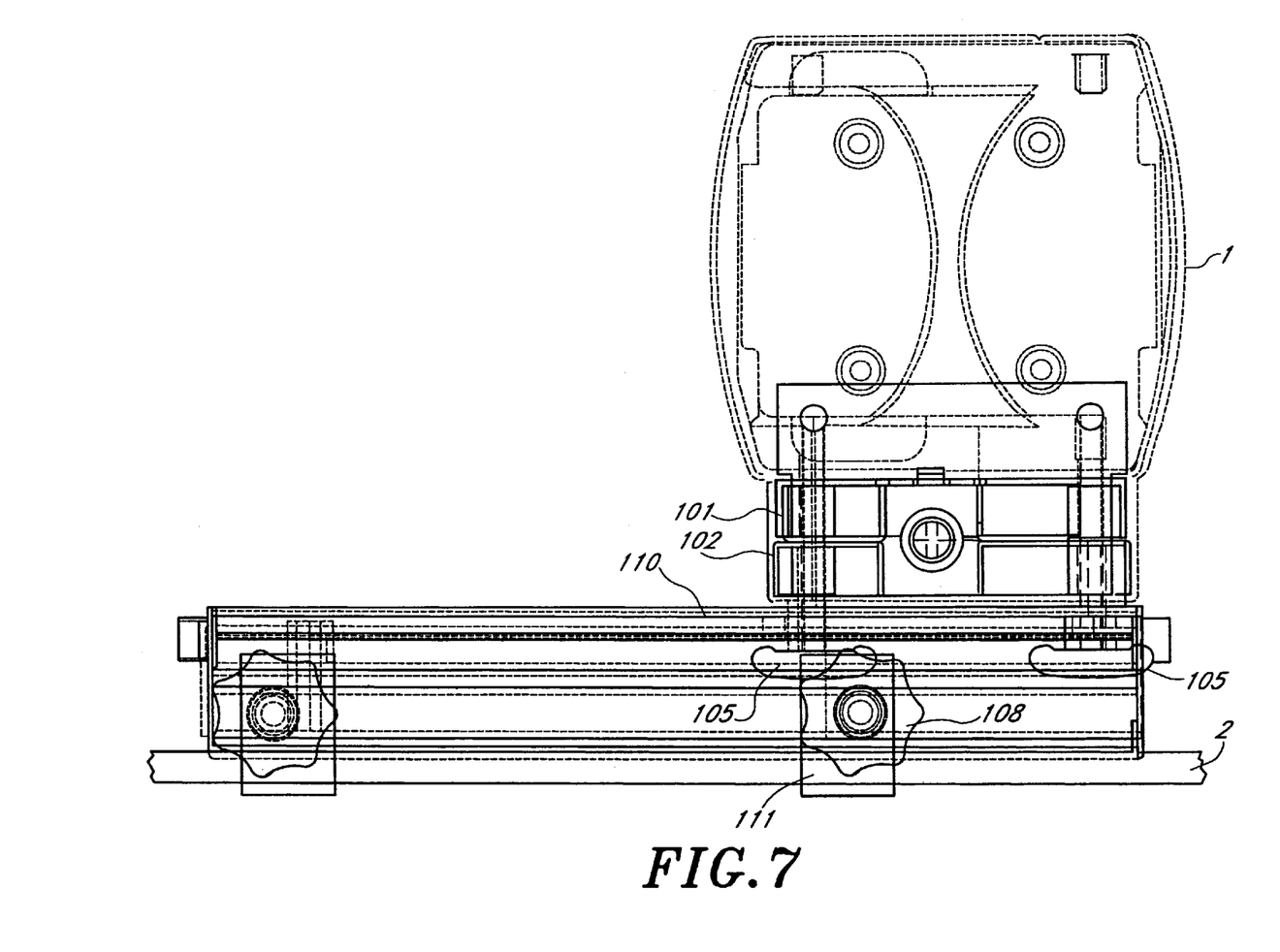
FIGS. 7 and 8 show a sectional side view and a sectional top view of a fastening device making it possible to fasten the handling device to the patient's bed according to a first embodiment.
Figure 8:
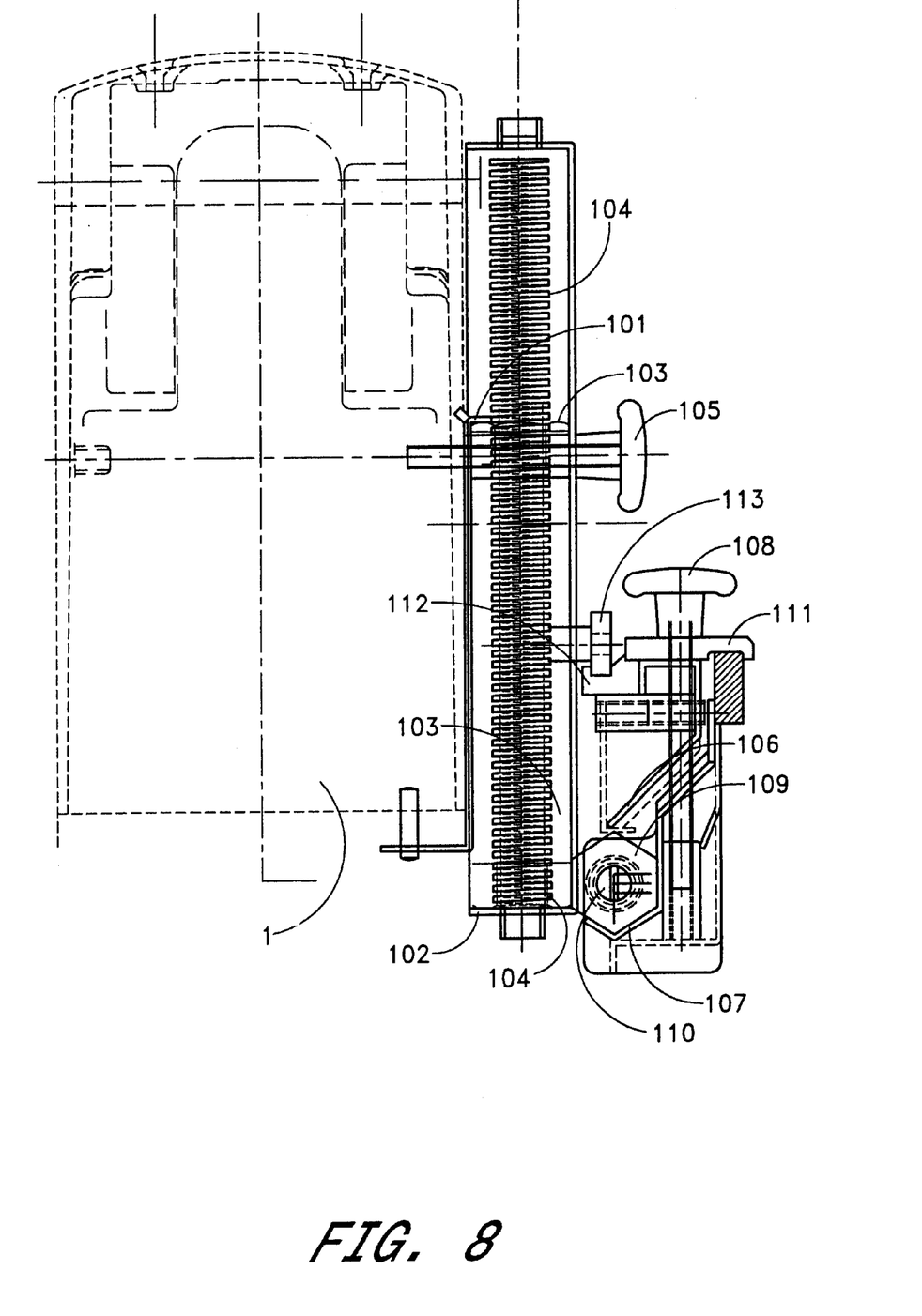

According to a first embodiment, a device (100) for fastening the handling device to the operating table is shown in FIGS. 7 and 8. This device (100) thus makes it possible accurately to adjust the position of the support (1) longitudinally (parallel to the rail (2) of the operating table (3)) and vertically (or, more generally, perpendicularly to the plane in which the patient is arranged).

This device comprises essentially two boxes (101 and 102) produced from metal sheets which are folded and welded to one another and closed, the purpose of which being to make the fastening of the device according to the invention more rigid. The first box (101) makes it possible to fasten the support (1) by the clamping of two knurled thumb screws (105). This box is integral with two nuts (103). A screw (104), which may be actuated manually or even be motorized, allows the box (101) to move within the second box (102) when the screw (104) is turned. This makes it possible to carry out the vertical movement. The originality of this device is the characteristic whereby the two boxes (101 and 102) slide with considerable play because they are produced with the aid of non-machined folded and welded metal sheets. This play will be cancelled by the entire assembly being fixed together particularly rigidly as a result of the clamping of the two knurled thumb screws (105) in the support (1) when the desired vertical position is reached.

The horizontal movement is carried out with the aid of the two nuts (109) integral with the box (102). A screw (110) makes it possible to displace the entire support (1), integral with the two boxes (101 and 102), parallel to the rail (2) of the operating table as far as the required position.

A box (106) likewise produced from folded and welded metal sheets, and which comprises two clamps (111) secured to the rail (2) of the operating table, is also provided. Rolling bearings (113) likewise fastened to the box (102) slide on a slideway (112) supporting the assembly consisting of the support (1) and of the boxes (101 and 102) during the longitudinal displacement. The originality of this device affords the possibility that, when the screw (108) is tightened, the rail (2) is clamped between the clamps (111) and the element (107). Simultaneously, the nuts (109) are locked between the box (106) and the same element (107), thus cancelling the considerable play of these non-machined components and thereby making the entire assembly particularly rigid.

Figure 9:
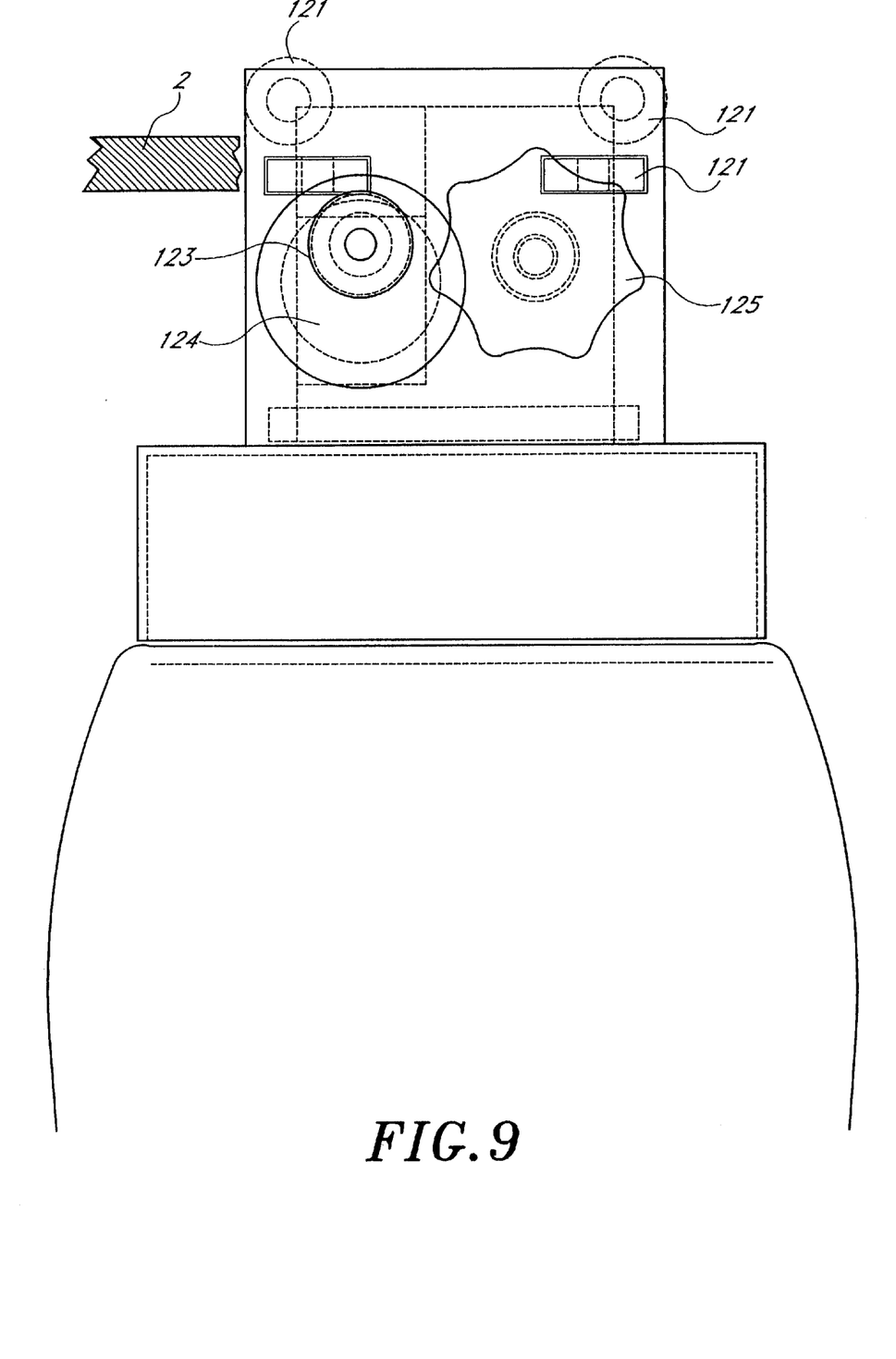
FIGS. 9, 10 and 11 show a second embodiment of the device for fastening the handling device to the patient's bed.
Figure 10:
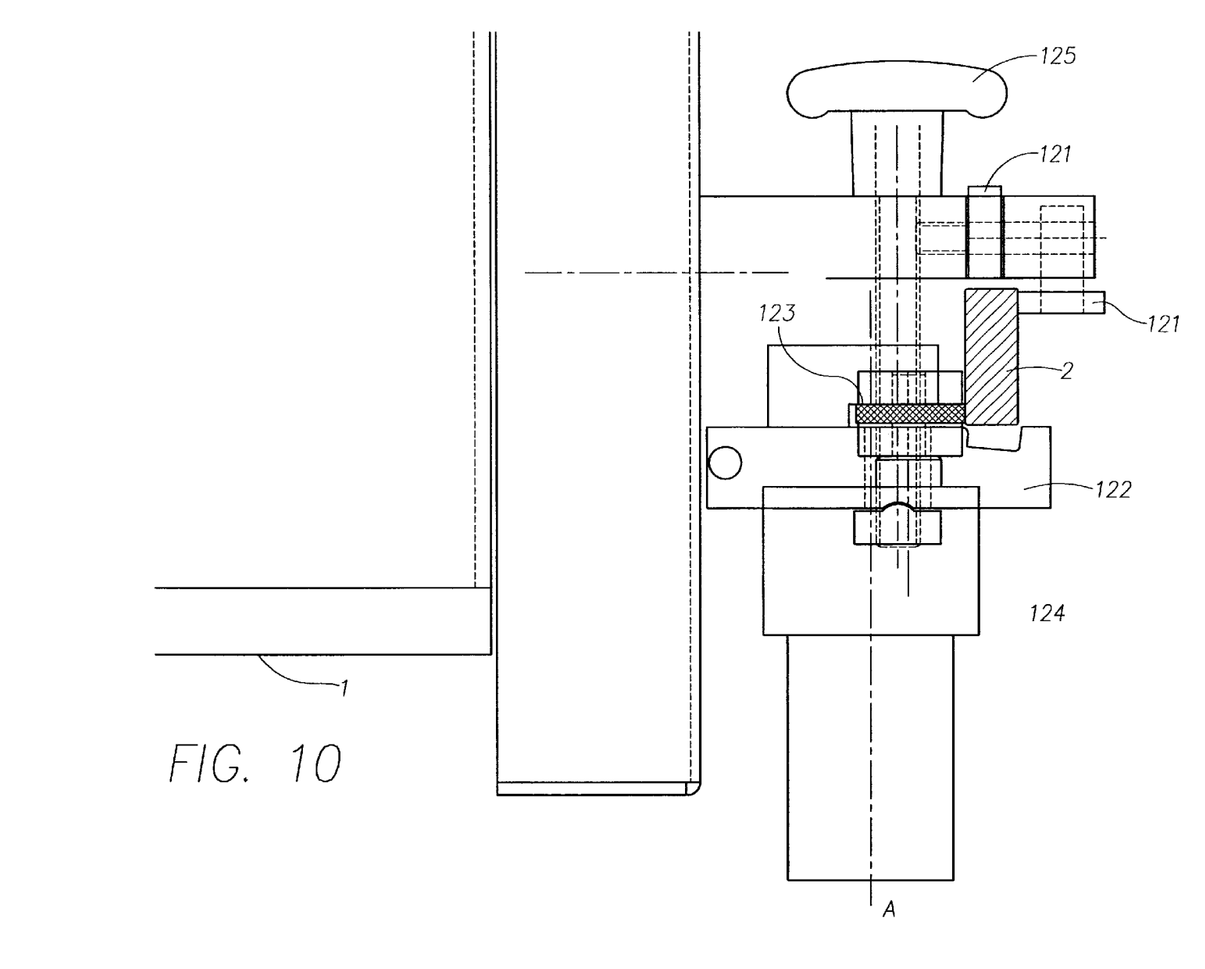
Figure 11:
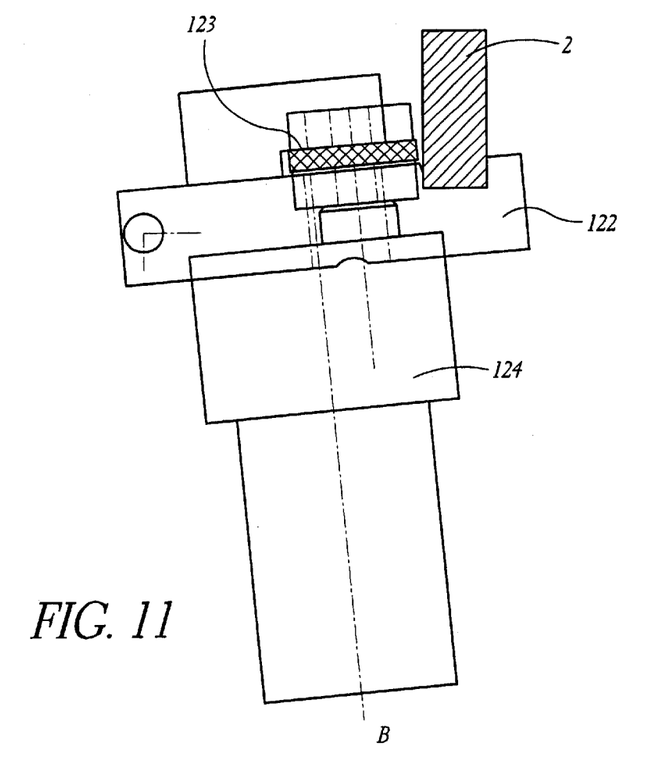

According to a second embodiment shown in more detail in FIGS. 9, 10 and 11, the rail (2) is used directly as a slideway by the provision of four orthogonal rolling bearings (121) in the upper part of the rail (2). When the lower clamp (122) is released (in position A, as shown in FIG. 10), the lower part of the rail (2) bears directly on a wheel (123) actuable by means of a geared motor (124). This wheel (123) allows displacement along the rail (2). When the lower clamp (122) is blocked by means of the wheel (125) and its screw (in position B, as shown in more detail in FIG. 11), the support assembly (1) will be completely immobilized, the geared motor (124) and its wheel (123) being disengaged.

What is claimed is:

1. A device for handling a surgical instrument, comprising:
   a fixed support;
   a first moveable element having a first end and a second end, the first moveable element at the first end being articulated on the fixed support about a first axis essentially parallel to a plane in which a patient is arranged and capable of executing a first movement;
   a second moveable element, having a first end and a second end, articulated on the second end of the first moveable element about a second axis essentially parallel to the plane in which the patient is arranged and capable of executing a second movement;
   a deformable element having a first side and a second side, the deformable element fastened on the first side to the second end of the second moveable element and capable of executing a third rotational movement about a third axis;
   a gripping element fastened to the second side of the deformable element;
   a securing device configured to secure a surgical instrument to the gripping element, and
   actuators configured to provide for rotational movements about said axes.

2. The device of claim 1, wherein the first and second moveable elements are articulated arms, and wherein the deformable element is a deformable and articulated quadrilateral.

3. The device of claim 2, wherein the second moveable element has a first point of articulation which can slide in a slideway integral with the deformable element, and wherein a second point of articulation can be blocked or unblocked.

4. The device of claim 1, wherein the gripping element is arranged in a slideway integral with the deformable element.

5. The device of claim 1, wherein the support element is fastened to a rail integral with an operating table through a fastening device.

6. The device of claim 5, wherein the fastening device comprises two boxes and provides for two movements, a movement orthogonal to the plane in which the patient is arranged and a movement parallel to the plane in which the patient is arranged, the orthogonal movement being carried out with the aid of a screw allowing the first box to be introduced into the second box, the longitudinal movement being carried out through a third box which comprises rolling bearings sliding on a slideway, the device being fastened when one or more screws are tightened, at the same time with the rail being clamped between clamps and a suitable element.

7. The device of claim 6, wherein the longitudinal movement is provided by a plurality of rolling bearings using the rail as a slideway, wherein a lower clamp and a wheel immobilize the device on the rail.

8. The device of claim 7, wherein the fastening device is reversed as a result of rotation about a vertical axis and adjusted by sliding along the rail.

9. The device of claim 1, wherein the securing device has a passive joint which comprises at least two components articulated along two axes perpendicular to an axis of the surgical instrument and to the axis of the first element, and in which the surgical instrument is fastened in a position such that a verticality reference of an image in the vertical plane is ensured.

10. The device of claim 1, further comprising a control device which includes a mini-keyboard with at least six keys and an inner part.

11. The device of claim 10, wherein the control device is completely independent and comprises a transmitter which transmits commands to the handling device.

* * * * *